United States Patent
Hiles et al.

(10) Patent No.: US 10,538,476 B2
(45) Date of Patent: Jan. 21, 2020

(54) PROCESS FOR CARRYING OUT A REACTION IN A REACTION COLUMN

(71) Applicant: JOHNSON MATTHEY DAVY TECHNOLOGIES LIMITED, London (GB)

(72) Inventors: Andrew George Hiles, London (GB); Rikard Umberto Andersson, London (GB); Michael Gavin John Williams, London (GB)

(73) Assignees: Johnson Matthey Davy Technologies Limited, London (GB); Johnson Matthey PLC, London (GB)

( * ) Notice: Subject to any disclaimer, the term of this patent is extended or adjusted under 35 U.S.C. 154(b) by 0 days.

(21) Appl. No.: 15/559,509

(22) PCT Filed: Mar. 17, 2016

(86) PCT No.: PCT/GB2016/050741
§ 371 (c)(1),
(2) Date: Sep. 19, 2017

(87) PCT Pub. No.: WO2016/151289
PCT Pub. Date: Sep. 29, 2016

(65) Prior Publication Data
US 2018/0118659 A1     May 3, 2018

(30) Foreign Application Priority Data

Mar. 24, 2015  (GB) .................................. 1504948.9

(51) Int. Cl.
*C07C 67/08*       (2006.01)
*B01D 3/00*        (2006.01)

(52) U.S. Cl.
CPC .............. *C07C 67/08* (2013.01); *B01D 3/007* (2013.01); *B01D 3/009* (2013.01)

(58) Field of Classification Search
CPC ........ B01D 3/007; B01D 3/009; B01D 3/346; C07C 67/08; C07C 29/149; C07C 31/125; C07C 31/207; C07C 69/24; C07C 69/60; Y02P 20/127; A61K 38/00; A61K 48/0016; A61K 48/005; A61P 7/04; C07K 14/755; C07K 2319/02; C07K 2319/30; C07K 2319/31; C12N 15/86; C12N 2740/15043; C12N 2740/16043; C12N 2800/22; C12N 7/00
See application file for complete search history.

(56) References Cited

U.S. PATENT DOCUMENTS

| | | | |
|---|---|---|---|
| 4,032,458 A | | 6/1977 | Cooley et al. |
| 5,302,305 A | * | 4/1994 | Jolley .................... C07F 9/4006 |
| | | | 508/427 |
| 5,536,856 A | * | 7/1996 | Harrison ................ B01D 3/163 |
| | | | 261/108 |
| 2002/0026070 A1 | * | 2/2002 | Bertola .................... C07C 67/08 |
| | | | 560/98 |
| 2012/0277481 A1 | | 11/2012 | Warner et al. |
| 2014/0364655 A1 | * | 12/2014 | Chen ..................... C07C 29/095 |
| | | | 568/877 |

FOREIGN PATENT DOCUMENTS

| | | | |
|---|---|---|---|
| CN | 201305565 | * | 9/2009 |
| WO | WO1988/00937 A1 | | 2/1988 |
| WO | WO1999/25678 | * | 5/1999 |

OTHER PUBLICATIONS

Lyon et al. (Methanol Recovery Optimization via Distillation, ChE 460 G.G. Brown Industries, Inc., published on the web Oct. 2012) Year: 2012).*
CN201305565 translated (Year: 2009).*
GB 1604549.4, Search and Examination Report dated Sep. 30, 2016.
PCT/GB2016/050741, International Search Report dated Jun. 1, 2016.

* cited by examiner

*Primary Examiner* — Yevgeny Valenrod
*Assistant Examiner* — Blaine G Doletski
(74) *Attorney, Agent, or Firm* — BakerHostetler

(57) ABSTRACT

A process for carrying out a reaction in a reaction column, said process comprising: providing a first reactant to the reaction column in the liquid phase; contacting said first reactant with an excess of a second reactant such that reaction takes place within the reaction column to form a low boiling product and a high boiling product, at least a portion of said second reactant being provided to the reaction column in the vapour phase; recovering an overhead stream from at, or near, the top of the reaction column, said overhead stream comprising unreacted second reactant and the low boiling product; and recovering a bottoms stream from at, or near, the bottom of the reaction column comprising the high boiling product; wherein at least a portion of the heat required to vaporise the second reactant provided to the reaction column in the vapour phase is provided by heat exchange in a heat exchanger with a hot stream generated within the process other than a hot stream generated within the reaction column.

21 Claims, 1 Drawing Sheet

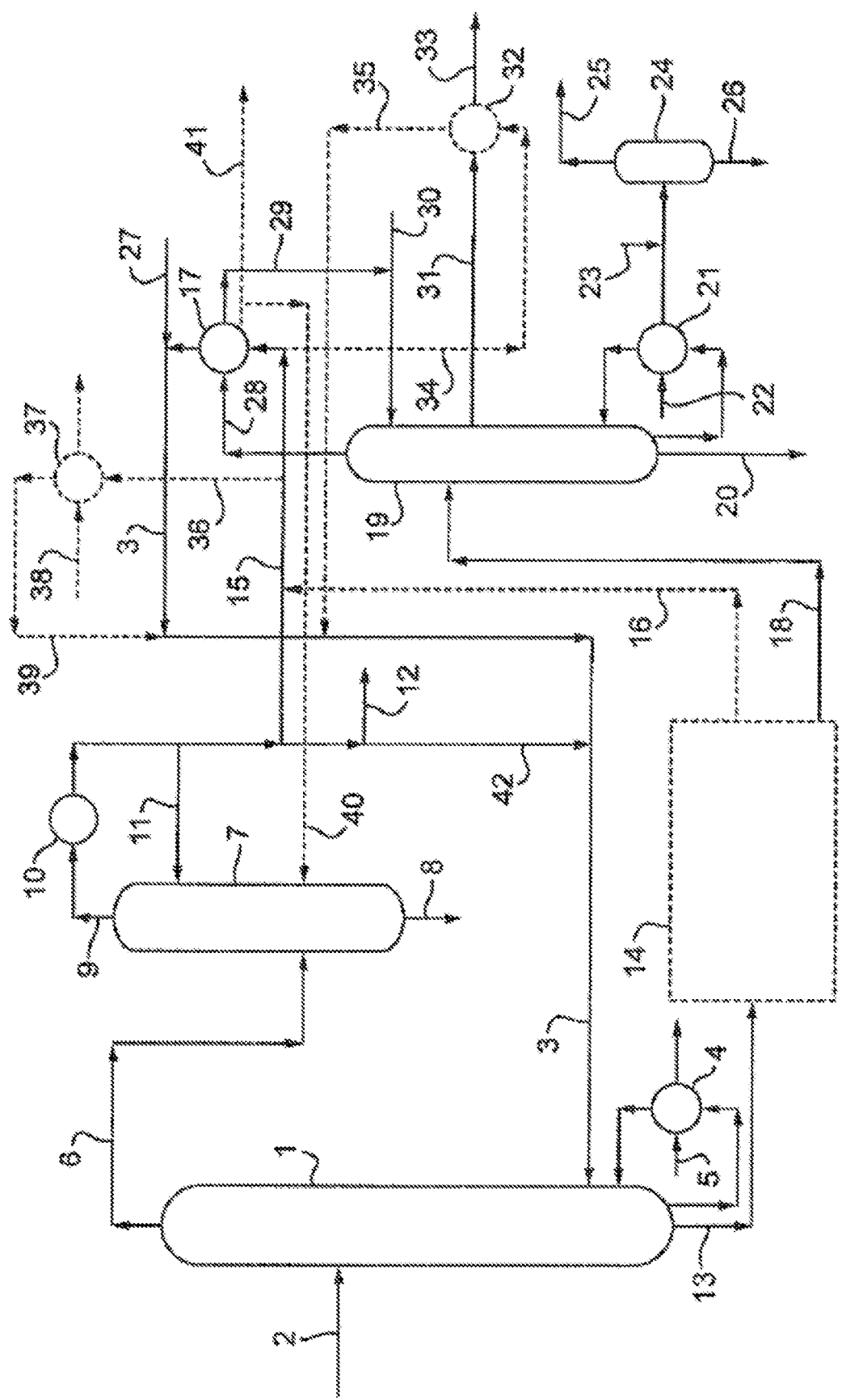

PROCESS FOR CARRYING OUT A REACTION IN A REACTION COLUMN

CROSS-REFERENCE TO RELATED APPLICATIONS

This application is a National Stage of International Patent Application No. PCT/GB2016/050741 filed Mar. 17, 2016, which claims the benefit of Great Britain Patent Application No. 1504948.9 filed Mar. 24, 2015, the disclosures of each of which are incorporated herein by reference in their entirety.

The present invention relates to a process for carrying out a reaction in a reaction column and in particular to the effective integration of the energy associated therewith. More particularly, it relates to a process for carrying out an esterification reaction in a reaction column.

A reaction column is one in which a reaction is carried out simultaneously with the separation of the primary product(s) from the secondary product(s) and/or in some circumstances, reactants. Such reaction columns and their use have been known for many years. Such reactions may not require the use of a catalyst but some reactions will require the use of a catalyst. Whether the catalyst is required and whether the catalyst, where present, is homogeneous or heterogeneous will depend on the reaction to be carried out. Reaction columns are particularly useful for carrying out reversible reactions in the liquid phase, for example esterification reactions. The benefit of using a reaction column is that the simultaneous separation of the primary product(s) from the secondary product(s) and/or reactant(s) drives the equilibrium such that the reaction can be moved towards completion. They are particularly useful for equilibrium limited reactions.

In processes carried out in reaction columns, one reactant will generally appear in the vapour phase. In this arrangement, some or all of this reactant may be provided in liquid phase but substantially all of it will vaporise within the column. This vapour phase reactant not only acts to provide a reactant but also acts to enhance mixing of the reactants, and to strip light secondary products from the reaction mixture which drives the liquid phase reaction towards completion.

One example of a reaction being carried out in a reaction column is described in U.S. Pat. No. 5,536,856. In the described process, esterification is carried out in a reaction column in which there is a plurality of esterification trays each of which has a predetermined liquid hold-up, each of which contains a charge of a solid esterification catalyst. A liquid phase containing the carboxylic acid reactant flows down the reaction column from one esterification tray to the next downward one against an upflowing alcohol vapour stream. Relatively dry alcohol is supplied to the bottom of the reaction column. Water of esterification is removed from the top of the reaction column in the vapour stream, whilst ester product is removed from the sump of the reaction column. Some of the alcohol vapour will condense on the trays to react with the carboxylic acid and as the liquid flows down the trays it encounters progressively drier alcohol and the esterification equilibrium reaction is driven toward completion.

Thus in this process, the alcohol vapour stream acts to provide a reactant, provides excess vapour for mixing the alcohol, the carboxylic acid and the solid catalyst on each stage while also serving to strip the water from the esterification reaction on each reaction tray thereby driving the reaction towards completion.

In U.S. Pat. No. 2002/026070, a similar approach is used although a homogeneous catalyst is used. An example of a similar process carried out in the absence of a catalyst can be found in U.S. Pat. No. 4,032,458.

Whilst these examples all relate to esterification reactions, it will be understood that such reaction columns may be used for a range of reactions.

Whatever reaction is being carried out, the amount of the vapour phase reactant required must be sufficient to provide a reactant, provide the required vapour for mixing the reactants and also strip the light secondary product and/or reactant. It will therefore be understood that substantially more vapour phase reactant will be required than the stoichiometric requirement for the reaction. In some cases, such as in esterification reactions, as much as two or three times the stoichiometric amount of vapour phase reactant will be required.

The product(s) removed from the reaction column may be subjected to further processing. For example, where the reaction is an esterification, the ester produced in the reaction column and removed in the stream from the column bottom may be further processed to produce other products. In one example, where the esterification reaction produces dialkyl maleate, the recovered dialkyl maleate stream may be subjected to hydrogenation to form 1,4-butanediol. Examples of this further reaction can be found in U.S. Pat. Nos. 4,584,419; 4,751,334 and WO88/00937. A further example of a subsequent reaction is described in U.S. Pat. No. 5,157,168 in which alkyl esters of fatty acids are hydrogenated to produce fatty alcohols.

Whilst the excess second reactant in the vapour phase will generally flow upwardly in the reaction column and be removed in the overhead stream, some will be retained and removed in the bottom stream which is generally in the liquid phase. Where the bottom stream is to be subjected to further reaction such as the hydrogenations discussed above, it is desirable to minimise the amount of second reactant in the product stream recovered from the bottom.

Thus where the reaction is an esterification reaction it is desirable to minimise the alcohol in the stream recovered from the bottom of the reaction column and hence in the ester being fed to the hydrogenation reaction. This is to minimise the contamination of downstream reaction systems with the alcohol which might otherwise form unwanted by-products. Additionally or alternatively, costs may have to be incurred in processing, recovering and recycling excess alcohol which is passed to these downstream process units. Where the ester has a high boiling point then heat exchange with typically medium pressure steam is required to minimise the alcohol content of the ester from the bottom of the reaction column.

It will be understood that in conventional processes for producing, for example, butanediol or fatty alcohols, one or more columns are required downstream of the hydrogenation reactor to distil the crude hydrogenation product to produce high purity products. Each of these columns will normally have condensers where the heat from the process is exchanged with cooling water. Thus this heat is essentially wasted from the distillation system.

As indicated above, other processes can be carried out in reaction columns. In these process, the products from the bottom of the reaction column may be subjected to further reactions and therefore the same issues apply as discussed above in needing to remove the excess reactant and the loss of heat produced in the system.

It should be noted that reaction columns are complex systems with multiple stages each allowing combined distillation and reaction. The mixing regimes and containment of the contents on individual trays, which may also contain catalyst, requires a high degree of stability in the operation of the reaction column.

The main problem associated with these reactions is that the large excess of the light reactant, such as the alcohol in the esterification reactions, requires a large amount of energy, normally in the form of steam, to vaporise this reactant. Conventionally, the heat required to vaporise the light reactant(s), for reaction, stripping and mixing purposes, would be provided using conventional utilities such as steam or hot oil as a heating medium in a heat exchanger. Whilst this is convenient, it has a high energy, and hence cost, requirement.

In addition, the need to minimise the amount of the light reactant in the product stream removed from the bottom of the reactor requires heat exchange with typically medium pressure steam. These factors increase the cost of processing and production of the esters or other products which will be fed to downstream processes, making the overall processes less energy efficient.

It is therefore desirable to provide a process for conducting reactions in a reaction column which seeks to address, and preferably overcome, some or all of these problems and in which energy is saved by the integration of streams from within the system and the transfer of heat therebetween.

This problem has been solved by the use of waste heat which would conventionally be discharged to cooling water and/or the use of low temperature waste steam which would otherwise be condensed by heat exchange with cooling water, to vaporise the light reactant which will form the vapour phase reactant to the reaction column.

Thus according to the present invention there is provided a process for carrying out a reaction in a reaction column, said process comprising:
  providing a first reactant to the reaction column in the liquid phase;
  contacting said first reactant with an excess of a second reactant such that reaction takes place within the reaction column to form a low boiling product and a high boiling product, at least a portion of said second reactant being provided to the reaction column in the vapour phase;
  recovering an overhead, stream from at, or near, the top of the reaction column, said overhead stream comprising unreacted second reactant and the low boiling product; and
  recovering a bottoms stream from at, or near, the bottom of the reaction column comprising the high boiling product;
  wherein at least a portion of the heat required to vaporise the second reactant provided to the reaction column in the vapour phase is provided by heat exchange in a heat exchanger with a hot stream generated within the process other than a hot stream generated within the reaction column.

In one arrangement, a major portion of the heat required to vaporise the second reactant is provided by heat exchange in a heat exchanger with a hot stream generated within the process. In one arrangement, at least 90% of the heat required to vaporise the second reactant is provided by heat exchange in a heat exchanger with a hot stream generated within the process. At least 92%, at least 95%, at least 97%, at least 99% may be provided by heat exchange in a heat exchanger with a hot stream generated within the process. In a further arrangement, substantially all of the heat required is provided by this means.

It will be understood that reference to a "high boiling product" and a "low boiling product" indicates their relative boiling points rather than a particular boiling point. Thus the high boiling product will have a boiling point that is higher than that of the low boiling product.

Thus at least a portion of the heat required to vaporise the second reactant is not provided from external heat sources. Thus the external energy requirement of the process is reduced. It will be understood that external heat may be required to vaporise the second reactant at start up. However, once the reaction is ongoing at least a portion of the heat required will be provided from within the process.

A benefit of the process of the present invention is that heat which is generated within the process and which is conventionally lost by being discharged to cooling water or which has to be condensed with cooling water is utilised thereby removing the requirements to arrange for this heat removal. The use of this heat generated within the process improves the economics of the overall process. Further, since less cooling water is required to deal with hot streams when compared to conventional processes, environmental advantages are also achieved.

Any suitable heat source or sources from within the process may be used to vaporise the second reactant other than a hot stream generated within the reaction column. In this connection it will be understood that the process from within which the hot stream is generated comprises the process as a whole and thus will include treatment of the streams recovered from the reaction column such as separation systems and further reactions. The 'hot stream' will be at any suitable temperature provided that it is at a temperature sufficient to allow vaporisation of the second reactant to occur.

Conventionally, it would not be generally thought possible to utilise these heat sources since it would be expected that they would not meet the stability requirements of the reaction column. Conventionally, it would be expected that the heat sources utilised in the present invention would be susceptible to long time lags and perturbations due to issues associated with the operation of the equipment in the part of the process from where the hot stream is derived. However, contrary to this conventional viewpoint, it has been found that such heat streams do meet the stability requirements of the reaction column. Indeed, in some circumstances, surprisingly it has been found that the use of heat sources from within the process can enhance the stability of the operation.

Indeed, without wishing to be bound by any theory, it is believed that when running the reboiler for the reaction column using conventional steam heating, pressure cycles can occur in the reaction column due to the differences in the relative volatility of the fluids involved. At high steam rates, a situation may arise where the second reactant boils very quickly and leaves the heavier product material behind. As this does not boil at the temperatures concerned, a much lower density difference is achieved in the reboiler than is required and the process flow slows down. This slowing down allows the second reactant to accumulate again. It is then vaporised. This reduction and subsequent increase in the amount of the second reactant present causes the pressure cycle in conventional systems.

In contrast, in the process of the present invention, by integrating the heat streams, a steadier supply of vaporised second reactant is provided, with the reaction column reboiler, where present, being used to provide fine tune and/or back-up control adjustment, which results in superior column stability.

At least a portion of the second reactant stream is provided to the reaction column in the vapour phase. Generally the major amount of the second reactant stream is provided to the reaction column in the vapour phase. In one arrangement, all of the second reactant stream is provided to the reaction column in the vapour phase. In this arrangement, the portion fed as liquid to the reaction column will generally be vaporised within the reaction column.

The vaporisation within the reaction column will generally be provided within the reaction column reboiler. The presence of the reboiler enables vaporisation to occur at start-up and provides an additional level of reaction column vapour flow and enables temperature control.

The second reactant stream may be unreacted second reactant recovered from the overhead stream optionally with make-up second reactant. In one arrangement, some or all of this recovered, second reactant may be fed to heat recovery units to be vaporised with the remainder being fed as liquid to the reaction column. Again, the portion fed as liquid to the reaction column will generally be vaporised within the reaction column.

Any suitable heat stream from within the process may be used to vaporise the second reactant. In one arrangement, the heat required to vaporise the second reactant is provided by heat exchange with a hot stream recovered from a distillation column. Any distillation column may be used. The distillation column may be one used to purify products. The hot stream recovered from the distillation column may be any stream. Thus it may be an overhead vapour stream, or in one alternative arrangement, it may be an internal column vapour stream.

Where the hot stream recovered from a distillation column is in vapour form, it will generally be condensed in the heat exchanger.

In one arrangement, the hot stream may be a hot liquid stream. The liquid stream may be generated by circulating a liquid stream over one or more packed beds which may be located at or near the top of a distillation column. In this arrangement, the circulated liquid acts as a direct contact condenser, or partial condenser, for a distillation column.

In one arrangement, the distillation column may be that used to separate the high boiling product in the bottoms stream either as directly recovered from the reaction column or having undergone one or more subsequent reactions. By 'subsequent reactions' we mean that the bottoms stream may have been treated after recovery from the reaction column before it is passed to the heat exchanger to provide heat to vaporise the second reactant.

The vaporisation of the second reactant may occur by passing the stream containing the second reactant in heat exchange with a vapour stream recovered from a distillation column in which the product in the bottoms stream, which may optionally have been the subject of one or more subsequent reactions, is separated such that the second reactant in the overhead stream is vaporised and the bottoms stream is cooled, the vaporised second reactant being provided to the reaction column.

Thus, in this arrangement, the vapour stream from the distillation column used to separate the bottoms product recovered from the column reactor provides the heat to vaporise the second reactant. Thus, for example, where the second reactant is an alkanol, such as methanol, since it has a low boiling point, it can be vaporised at a relatively low temperature and can utilise heat from process streams which would otherwise normally be cooled and condensed by cooling water.

The heat exchanger used to vaporise the second reactant may be a sole heat removal unit on the distillation column. However, in one arrangement, it may be one of a plurality of heat removal units. Thus, in one arrangement, a second and, where present, subsequent heat removal units, may be utilised to raise steam or to discharge heat to cooling water. In one alternative arrangement, a plurality of heat removal units may be used to vaporise the second reactant at different temperatures and/or pressures to maximise the utilisation of heat from the distillation column overhead stream. In this arrangement, the second reactant at different temperatures and/or pressures may be fed to different locations in the reaction column. Thus whilst one stream of vaporised second reactant will generally be provided at, or near, the bottom of the reaction column, other streams may be fed optionally to locations partially up the reaction column to integrate with the raised pressure of the second reactant.

This arrangement, allows for different purity streams of second reactant to be accommodated by feeding to the appropriate location within the reaction column.

Additionally, or alternatively, the vaporisation of the second reactant may occur by passing the stream containing the second reactant in heat exchange with a hot product draw stream removed from the distillation column which is used to separate the high boiling product in the bottoms stream either as directly recovered from the reaction column or having undergone one or more subsequent reactions.

Additionally, or alternatively, the vaporisation of the second reactant may occur by passing the stream containing the second reactant in heat exchange with steam which has been flashed from waste condensate streams at, or near, atmospheric pressure. It will be understood that the process will include a variety of heat exchangers such as column reboilers and the heat from this condensate or the flash steam generated from the condensate is often wasted. Although in conventional systems this would have no use as a heating medium it can be utilised in the present invention to vaporise the second reactant which is subsequently fed to the column reactor.

The process of the present invention may include one hot stream to vaporise all of the second reactant. Alternatively, a plurality of hot streams may be used. These hot streams may be combined and fed to the same heat exchanger or two or more separate heat exchangers may be used. Where two or more separate exchangers are present, they may be placed in series such that the subsequent heat exchangers provide further contact with hot streams. This may enable additional second reactant to be vaporised. Thus the heat exchangers may be cascaded such that the bubble point liquid which is not vaporised in one exchanger is sent to another exchanger for further vapour generation.

Alternatively, the two or more separate heat exchangers may be situated on separate second reactant streams. These may be arranged in parallel or may be located in separate parts of the process. This offers the advantage of allowing the bubble point temperature and hence the temperature approach to the condensing process fluid to be manipulated.

The heat exchanger used to enable the heat recovered from the vapour recovered from the distillation column to be used to vaporise the second reactant can be of any suitable configuration. Generally it will be designed to condense the vapour from the distillation column and for boiling the second reactant.

Whichever hot stream is used to vaporise the second reactant, the overhead stream comprising second reactant may be passed to a separator where the low boiling product is separated from the second reactant stream before the second reactant is passed to the heat exchanger(s).

Whichever system is used, the heat exchanger may include a control system which may include a pressure control which will allow the pressure to be varied as the second reactant is vaporised. This has the advantage of allowing the bubble point temperature and hence the temperature approach to the condensing process fluid to be manipulated. This ability to control and vary the pressure at which the second reactant is vaporised could also be used to help manage any operational fluctuations which may occur between the heat exchanger and the reaction column.

Howsoever vaporised, the vapour generated may be fed directly to the reaction column without the need for intermediate heat exchangers or any other vessels or pumps. Thus the process of the present invention reduces capital and operation costs.

In one arrangement of the present invention, as the second reactant is vaporised, an impure second reactant stream may be flashed from the second reactant stream. The purer second reactant can then be passed to the reaction column while the impure stream may be removed, for example in a purge stream.

The present invention is particularly suitable for the production of an ester. In this arrangement, the first reactant will be a carboxylic acid and the second reactant will be an alcohol. In this process, a catalyst may be used.

In an esterification reaction, the overhead stream comprises unreacted alcohol and the low boiling product will be water. The bottom stream will comprise the product ester. It will also generally include some unreacted alcohol.

More particularly the process of the present invention may be a process for the production of carboxylic acid esters by reaction of a carboxylic acid component selected from mono-, di- and polycarboxylic acids, anhydrides thereof, and mixtures thereof, and of an alcohol component selected from mono-, di- and polyhydric alcohols, phenols, and mixtures thereof, in the presence of a solid esterification catalyst selected from particulate ion exchange resins having sulphonic groups, carboxylic groups or both.

Examples of monoesterification reactions include the production of alkyl esters of aliphatic monocarboxylic acids from alkanols and aliphatic monocarboxylic acids or anhydrides thereof. Such monocarboxylic acids may contain, for example, from about 6 to about 26 carbon atoms and may include mixtures of two or more thereof.

Alkyl esters derived from alkanols containing 1 to about 10 carbon atoms may be of particular importance. Any suitable alkanol can be used. Short chain, low boiling alkanols such as methanol and ethanol may offer advantages.

Such monocarboxylic acids include fatty acids such as decanoic acid, dodecanoic acid, tetradecanoic acid, hexadecanoic acid, octadecanoic acid, linoleic acid, eicosanoic acid, isostearic acid and the like, as well as mixtures of two or more thereof. Mixtures of fatty acids are produced commercially by hydrolysis of naturally occurring triglycerides of vegetable origin, such as coconut oil, rape seed oil and palm oils, and triglycerides of animal origin, such as lard, tallow and fish oils. If desired, such mixtures of acids can be subjected to distillation to remove lower boiling acids having a lower boiling point than a chosen temperature (e.g. $C_8$ to $C_{10}$ acids) and thus produce a "topped" mixture of acids, or to remove higher boiling acids having a boiling point higher than a second chosen temperature (e.g. $C_{22+}$ acids) and thus produce a "tailed" mixture of acids, or to remove both lower and higher boiling acids and thus produce a "topped and tailed" mixture of acids. Such fatty acid mixtures may also contain ethylenically unsaturated acids such as oleic acid. These fatty acid mixtures can be esterified with methanol to yield methyl fatty acid ester mixtures that can be hydrogenated to yield mixtures of alkanols, e.g. $C_8$ to $C_{20}$ alkanols (often called detergent alcohols), that are acceptable for production of detergents without prior separation of alkanols one from another.

Another class of carboxylic acid esters that can be produced by the process of the invention are dialkyl esters of aliphatic and cycloaliphatic $C_4$ to $C_{18}$ saturated and unsaturated dicarboxylic acids. These can be produced by reaction of alkanols with the dicarboxylic acids or anhydrides thereof, or with mixtures of the dicarboxylic acid and its anhydride. Dialkyl oxalates, dialkyl maleates, dialkyl succinates, dialkyl fumarates, dialkyl glutarates, dialkyl pimelates, and dialkyl azelaates are examples of such dicarboxylic acid esters. Other examples of such esters include dialkyl esters of tetrahydrophthalic acid. The $C_1$ to $C_{10}$ alkyl esters of such dicarboxylic acids are of particular interest. Either the free dicarboxylic acid or its anhydride, if such exists, or a mixture of dicarboxylic acids and anhydride can be used as the carboxylic acid component starting material for production of such dialkyl esters. Alkyl esters of aromatic $C_7$ to $C_{20}$ monocarboxylic acids and mixtures thereof can be made by a process of the invention. Benzoic acid and 1-naphthoic acid are examples of such acids.

Alkyl esters of aromatic $C_8$ to $C_{20}$ dicarboxylic acids can also be produced by the process of the invention from the acids, their anhydrides and mixtures thereof.

It is also possible to produce polyalkyl esters of polycarboxylic acids by the process of the invention. Such polycarboxylic acid moieties include, for example, citric acid, pyromellitic dianhydride, and the like.

Carboxylic acid esters of dihydric and polyhydric alcohols can be produced by the process of the invention. Examples of such esters include ethylene glycol diformate, ethylene glycol diacetate, propylene glycol diformate, propylene glycol diacetate, glyceryl triacetate, hexose acetates, and the acetate, propionate and n-butyrate esters of sorbitol, mannitol and xylitol, and the like.

Further examples of reactions which can be carried out in the process of the present invention include, but are not limited to:
  the formation of pyrrolidines such as from succinates or from lactones such as γ-butyrolactone;
  transesterifications such as the formation of aromatic carbonates from dialkyl carbonate and an aromatic monohydroxy compound, the formation of alkanediol and a dialkyl carbonate from alkylene carbonate and an alkanol, the formation of diaryl carbonate esters by reaction of a dialkyl carbonate and the reaction of an aromatic alcohol to form a diaryl carbonate and an alkyl alcohol, such transesterifications being carried out in an extractive/reactive distillation column in the presence of a transesterification catalyst;
  the production of epoxides from aqueous alkali and halohydrin;
  the production of acetates from acetic acid;
  the production of polyamides;
  the production of dioxylane from ethylene glycol and an aqueous formaldehyde solution;
  propylene oligomerization such as that using a tungstated zirconia catalyst;
  the production of cumene from benzene and propylene using a column packed with a solid acid zeolite catalyst;

the production of diethylenetriamine (DETA), by continuous reaction of ethylenediamine (EDA) in the presence of a heterogeneous catalyst;

the alkylation of light aromatic hydrocarbons such as benzene with $C_2$-$C_{30}$ olefins using a solid acid alkylation catalyst;

the production of monochloroacetic acid from chlorine and acetic acid;

the production of dimethylformamide by reacting methyl formate and dimethylamine;

hydrolysis reactions such as the production of esters, primary and secondary amides and halogenalkanes;

etherification reactions such as the production of methyl t-buty ether (MTBE) and ethyl t-butyl ether (ETBE); and olefin metathesis.

The identity of the low boiling product and the high boiling product will depend on the reaction being carried out. However, generally the low boiling product will be a secondary product and the high boiling product will be a primary product.

Feeds to the process of the present invention can be derived from any suitable source and may be obtained by petrochemical routes and/or by biochemical routes such as the fermentation of sugars.

The operation conditions of the reaction column will depend on the reaction being carried out. Where the reaction is an esterification the normal boiling point range of the light reactant used will generally be in the region of about 50° to about 200° C. and the normal boiling range of the high boiling product is in the region of about 130° C. to about 400° C.

The present invention will now be described by way of example with reference to the following drawing in which:

The FIGURE is a schematic representation of one embodiment of the process of the present invention.

It will be understood that the drawing is diagrammatic and that further items of equipment such as reflux drums, pumps, vacuum pumps, temperature sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

For convenience, the present invention will be specifically described with reference to the esterification of a carboxylic acid with an alcohol and in particular where the alcohol is methanol. However it will be understood that it applies equally to other processes.

A liquid feed 2 of first reactant (in this example the carboxylic acid) is supplied to the reaction column 1 where it flows downwardly through the reaction column 1 against upflowing vapour of the second reactant, (in this example methanol), which is added to the reaction column 1 in line 3. Additional second reactant 42 may be added to the reaction column 1 in the liquid phase which is vaporsied in the reboiler 4. The reaction column 1 may be of any suitable configuration but may include a plurality of trays each of which has a predetermined liquid hold-up, and contains a catalyst where required (where the reaction is an esterification, each of the trays contains a charge of a solid esterification catalyst). The second reactant in the vapour phase (in this example methanol) provided to the trays, mixes the first reactant (carboxylic acid) and the catalyst and strips the low boiling product (which in the case of esterification will be water). As the first reactant (in this example carboxylic acid) flows down through the trays it contacts progressively drier second reactant (in this example methanol).

The excess second reactant (e.g. methanol) and the low boiling product (e.g. water) are then removed in the overheads stream 6 from the reaction column 1. The reaction column 1 will generally include a reboiler 4 which may include heat exchange with a high pressure steam added in line 5. The low boiling product, (e.g. water), together with the excess second reactant (e.g. methanol), is removed as overheads in line 6 and passed to a separation column 7. The light product (e.g. water) is removed from the bottom of the separation column 7 in line 8.

The second reactant (e.g. methanol) will leave the column in line 9 and be condensed in condenser 10. Some condensed second reactant (e.g. methanol) will be returned to the top of the separation column 7 in line 11 as reflux.

The high boiling product (e.g. the ester), is recovered from the reaction column 1 in line 13 and may optionally be subjected to further reaction (e.g. hydrogenation) in reactor 14. The crude product stream is then passed in line 18 to a product purification column 19. The hot overhead from the product purification column 19 is removed in line 28 and passed to a first heat exchanger 17 where it is passed in counter-current heat exchange with the liquid second reactant (methanol) which is not returned to the separation column 7 in line 11 but passed to the first heat exchanger 17 in line 15. Further second reactant (methanol) may be passed to other condensers (not shown) in line 12.

The liquid second reactant (methanol) is vaporised in the first heat exchanger 17 against the hot stream in line 28 from the product purification column 19. The vaporised second reactant (e.g. methanol) is the stream fed to the reaction column 1 in line 3. Vaporised second reactant (e.g. methanol) from other condensers can be fed in line 27 into the stream added to the reaction column 1 in line 3.

In the first heat exchanger 17 vapour in hot stream 28 is cooled and condensed and may be returned to the column 19 as reflux in line 29. Some may be recovered in line 30.

Optionally, bubble point light reactant liquid may be passed to other heat exchangers, not shown, for vaporisation in line 41. Optionally, additionally or alternatively, at least some of the bubble point light reactant liquid (e.g. comprising water and methanol) may be returned in line 40 to the separation column 7. In one option, a portion of the light second reactant (e.g. methanol) liquid recovered from the condenser 10 is passed in line 36 to a second heat exchanger 37 where it is vaporised against hot flash steam 38. The vaporised second reactant (e.g. methanol) is added in line 39 to the stream 3 added to the reaction column 1.

Optionally, second reactant (e.g. methanol) recovered from the optional further reaction in reactor 14 may be removed in line 16 and added to the stream passed to the first heat exchanger 17 in line 15 to be vaporised.

In an alternative arrangement, a portion of the light second reactant (e.g. methanol) may be passed in line 34 to a third heat exchanger 32 where it is vaporised against hot product removed from the product purification column 19. The vaporised second reactant (e.g. methanol) may then be passed in line 35 to the vaporised second reactant stream 3 fed to the reaction column 1. In the third heat exchanger 32 the hot product in stream 31 is cooled and then recovered in line 33.

The product purification column 19 may include a reboiler 21 where a bottom stream is heated against steam added in line 22. The steam is condensed in the reboiler 21. The condensate may have other condensates from elsewhere in the system added in line 23. These are passed to a separator 24. Flash steam may be recovered in line 25 and liquid in line 26. Column bottoms are removed in line 20. The flash stream in line 25 can be used to vaporise further methanol via line 38 in condenser 37.

Any second reactant from condenser 10 not vaporised can be returned to the reaction column 1 via lines 42 and 3 to be vaporised in reboiler 4. In one arrangement, the stream may be fed to the reactor separate from line 3.

The present invention will now be described with reference to the accompanying examples.

EXAMPLE 1

In a process to produce 1,4 butanediol from maleic anhydride the maleic anhydride is esterified first in an autocatalytic reactor in contact with methanol, in a near to stoichiometric ratio to produce a stream of mono methyl maleate and heated to a temperature of about 110° C. This stream is fed near to the top of a reaction column containing a solid esterification catalyst suspended on the column reaction trays. Dry methanol is fed to the bottom of the reaction column at a feed rate equivalent to about 3 mols of methanol to each mol of maleic anhydride feed. The methanol is vaporised in the reboiler which is heated by steam at a pressure of about 20 barg. This methanol travels up the column as a vapour, mixing and suspending the resin on the reaction trays, stripping water from the reaction trays and partially condensing on the trays to react with the mono methyl maleate to form dimethyl maleate and water. The conversion to dimethyl maleate is >99%. The bottom offtake liquid is heated up to about 160° C. in the reboiler which reduces the methanol content of the bottom liquid to <5 wt %. The overhead vapour from the reaction column containing the excess methanol and water from the esterification reaction is fed to a distillation column (the methanol column) to remove the water from this stream and produce a dry methanol stream for recycle to the reaction column bottom. The dimethyl maleate is fed to a hydrogenation reaction system for conversion to a mixture of 1,4 butanediol and co-products of tetrahydrofuran and [gamma]-butyrolactone. These are separated from each other, from other impurities and from methanol and water produced in hydrogenation in a series of distillation columns to produce product grade 1,4 butanediol, tetrahydrofuran and [gamma]-butyrolactone. In this arrangement the steam requirement for the reaction column reboiler is about 0.7 ton of steam per ton of total products.

EXAMPLE 2

In a process similar to that of Example 1, one of the distillation columns used in the purification of the 1,4 butanediol product is arranged to operate at a pressure which gives an overhead condensing temperature of about 100-150° C. About 65% of the dry methanol produced in the methanol column is fed to the shell side of this condenser and exchanges heat with the condensing tube side fluid which boils the methanol at a temperature of about 80-90° C. This methanol vapour is fed to the reaction column and the remaining dry methanol is fed to the reaction column and vaporised in the reaction column reboiler. In this arrangement the steam requirement for the reaction column reboiler is about 0.3 ton of steam per ton of total products.

EXAMPLE 3

In a process similar to that of Example 1, one of the distillation columns used in the purification of the γ-butyrolactone product is arranged to operate at a pressure which gives an overhead condensing temperature of about 100-130° C., as well as the column used in the purification of the 1,4 butanediol product. A total of about 90% of the dry methanol produced in the methanol column is fed to the shell side of these two condensers and exchanges heat with the condensing tube side fluid which boils the methanol at a temperature of about 80-90° C. This methanol vapour from both condensers is fed to the reaction column and the remaining dry methanol is fed to the reaction column and vaporised in the reaction column reboiler. In this arrangement the steam requirement for the reaction column reboiler is about 0.25 ton of steam per ton of total products.

EXAMPLE 4

In a process to produce medium cut natural detergent alcohol (MCNDA) from fatty acids, the pre-distilled medium cut fatty acids are heated to a temperature of about 120° C. This stream is fed near to the top of a reaction column containing a solid esterification catalyst suspended on the column reaction trays. Dry methanol is fed to the bottom of the reaction column at a feed rate equivalent to about 3 mols of methanol to each mol of fatty acid feed. The methanol is vaporised in the reboiler which is heated by steam typically in the pressure range 5 to 15 barg. This methanol travels up the column as a vapour, mixing and suspending the resin on the reaction trays, stripping water from the reaction trays and partially condensing on the trays to react with the fatty acid to form fatty acid methyl ester and water. The conversion to fatty acid methyl ester is >99%. The bottom offtake liquid is heated up to about 130° C. in the reboiler which reduces the methanol content of the bottom liquid to <5 wt %. The overhead vapour from the reaction column containing the excess methanol and water from the esterification reaction is fed to a distillation column (the methanol column) to remove the water from this stream and produce a dry methanol stream for recycle to the reaction column bottom. The fatty acid methyl ester is fed to a hydrogenation reaction system for conversion to fatty alcohol. The crude fatty alcohol product is then treated and distilled to separate out light and heavy impurities in a refining column, prior to product polishing to produce product grade MCNDA. A hot oil system is typically used to provide reboil to the refining column due to the low volatility of the fatty alcohol. In this arrangement the steam requirement for the reaction column reboiler is about 0.35 ton of steam per ton of MCNDA.

EXAMPLE 5

In a process similar to that of Example 5, the refining columns used in the purification of the crude fatty alcohol product is arranged to operate at a pressure which gives an overhead condensing temperature of about 120-140° C. About 60-90% of the dry methanol produced in the methanol column is fed to the shell side of the overhead condenser and exchanges heat with the condensing tube side fluid which boils the methanol at a temperature of about 95-105° C. This methanol vapour is fed to the reaction column and a fraction of the remaining dry liquid methanol is fed to the reaction column and vaporised in the reaction column reboiler. In this arrangement the steam requirement for the reaction column reboiler is about 0.06 ton of steam per ton of MCNDA.

EXAMPLE 6

In the processes described in, Examples 4 and 5 there is a short term interruption to the steam supply due to a trip on the steam letdown system. For Example 4 this leads to a rapid loss of methanol vapour up flow in the reaction column and it is necessary to stop feeding acid to the plant until after the steam supply is restored.

For Example 5 there is only a relatively small drop off in methanol vapour up flow in the reaction column and by reducing the feed rate of acid to 70% of normal, the plant is able to maintain steady production of fatty alcohol at a reduced rate. The plant is also in a ready state to rapidly return to 100% capacity when the steam supply is restored.

The invention claimed is:

1. A process for carrying out a reaction in a reaction column, said process comprising:
    providing a first reactant to the reaction column in the liquid phase;
    contacting said first reactant with an excess of a second reactant such that reaction takes place within the reaction column to form a low boiling product and a high boiling product, a portion of said second reactant being provided to the reaction column in a vapour phase and another portion of said second reactant is provided to the reaction column as liquid;
    recovering an overhead stream from at, or near, the top of the reaction column, said overhead stream comprising unreacted second reactant and the low boiling product; and
    recovering a bottoms stream from at, or near, the bottom of the reaction column comprising the high boiling product,
    wherein at least a portion of the heat required to vaporise the portion of the second reactant that is provided to the reaction column in the vapour phase is provided by heat exchange in a heat exchanger with a hot stream that is generated within the process, but that is not generated within the reaction column;
    and,
    wherein the portion of the second reactant that is fed as liquid to the reaction column is vaporised within a reboiler of the reaction column.

2. The process according to claim 1, wherein the hot stream is an overhead vapour stream or an internal column vapour stream.

3. The process according to claim 1, wherein the hot stream is a hot liquid stream generated by circulating a liquid stream over one or more packed beds in a distillation column.

4. The process according to claim 1, wherein the distillation column is used to purify products.

5. The process according to claim 4, wherein the distillation column is used to separate the high boiling product in the bottoms stream as directly recovered from the reaction column.

6. The process according to claim 4, wherein the distillation column is used to separate the high boiling product in the bottoms stream after the bottoms stream undergoes one or more subsequent treatments.

7. The process according to claim 1, wherein the heat exchanger used to vaporise the second reactant is a sole heat removal unit on a distillation column.

8. The process according to claim 1, wherein the heat exchanger used to vaporise the second reactant is one of a plurality of heat removal units.

9. The process according to claim 8, wherein a second and, where present, subsequent heat removal units, are utilised to produce steam or discharge heat to cooling water.

10. The process according to claim 8, wherein two or more heat removal units are used to vaporise the second reactant at different temperatures and/or pressures.

11. The process according to claim 10, wherein the vaporised second reactant at different temperatures and/or pressures is fed to different locations in the reaction column.

12. The process according to claim 1, wherein the vaporisation of the second reactant occurs by passing the stream containing the second reactant in heat exchange with a hot product draw stream removed from a distillation column which is used to separate the high boiling product in the bottoms stream that is either directly recovered from the reaction column or that has undergone one or more subsequent treatments.

13. The process according to claim 1, wherein the vaporisation of the second reactant may occur by passing the stream containing the second reactant in heat exchange with steam which has been flashed from waste condensate streams at or near atmospheric pressure.

14. The process according to claim 1, wherein one hot stream is used to vaporise at least a portion of the second reactant.

15. The process according to claim 1, wherein a plurality of hot streams is used to vaporise at least a portion of the second reactant.

16. The process according to claim 15, wherein the plurality of hot streams are combined and fed to the same heat exchanger.

17. The process according to claim 15, wherein the plurality of hot streams are fed to two or more separate heat exchangers.

18. The process according to claim 15, wherein the two or more separate exchangers are in series.

19. The process according to claim 15, wherein the two or more separate heat exchangers are located on separate second reactant streams.

20. The process according to claim 1, wherein the heat exchanger includes a control system which includes a pressure control which will allow the pressure to be varied as the second reactant is vaporised.

21. The process according to claim 1, wherein the process is an esterification reaction.

* * * * *